United States Patent [19]

Bertelsen

[11] Patent Number: 5,060,317
[45] Date of Patent: Oct. 29, 1991

[54] COMBINATION SPECIMEN CUP AND BRACKET

[76] Inventor: Erik Bertelsen, 1251 Easthill Crt., Mobile, Ala. 36695

[21] Appl. No.: 513,897

[22] Filed: Apr. 24, 1990

[51] Int. Cl.$^5$ .............................................. A47K 11/00
[52] U.S. Cl. ...................................... 4/144.2; 422/103
[58] Field of Search ................ 128/760, 761, 764, 771; 4/661, 684, 144.2; 73/863.52; 422/103; 215/DIG. 3; 248/227, 311.2

[56] References Cited

U.S. PATENT DOCUMENTS

| | | | |
|---|---|---|---|
| 3,137,010 | 6/1964 | Ross | 4/483 |
| 3,466,145 | 9/1969 | Van Duyne | 4/661 |
| 3,625,654 | 12/1971 | Van Duyne | 128/760 |
| 4,309,782 | 1/1982 | Paulin | 4/661 |
| 4,408,905 | 10/1983 | Ehrenkranz | 128/761 |
| 4,466,445 | 8/1984 | Abrams | 128/761 |
| 4,749,112 | 6/1988 | Harper | 248/311.2 |
| 4,832,046 | 5/1989 | Parrish | 128/771 |

Primary Examiner—Henry J. Recla
Assistant Examiner—Scott Flanders
Attorney, Agent, or Firm—Nixon & Vanderhye

[57] ABSTRACT

A disposable specimen cup and bracket for holding the same comprising a bracket with bendable arms designed to fit over the rim of a toilet bowl and extending into the toilet bowl and having a hole for receiving a sample cup which funnels fluids to the center and is designed to sit upright on a stand or within the bracket hole when the bracket is within the toilet bowl.

32 Claims, 3 Drawing Sheets

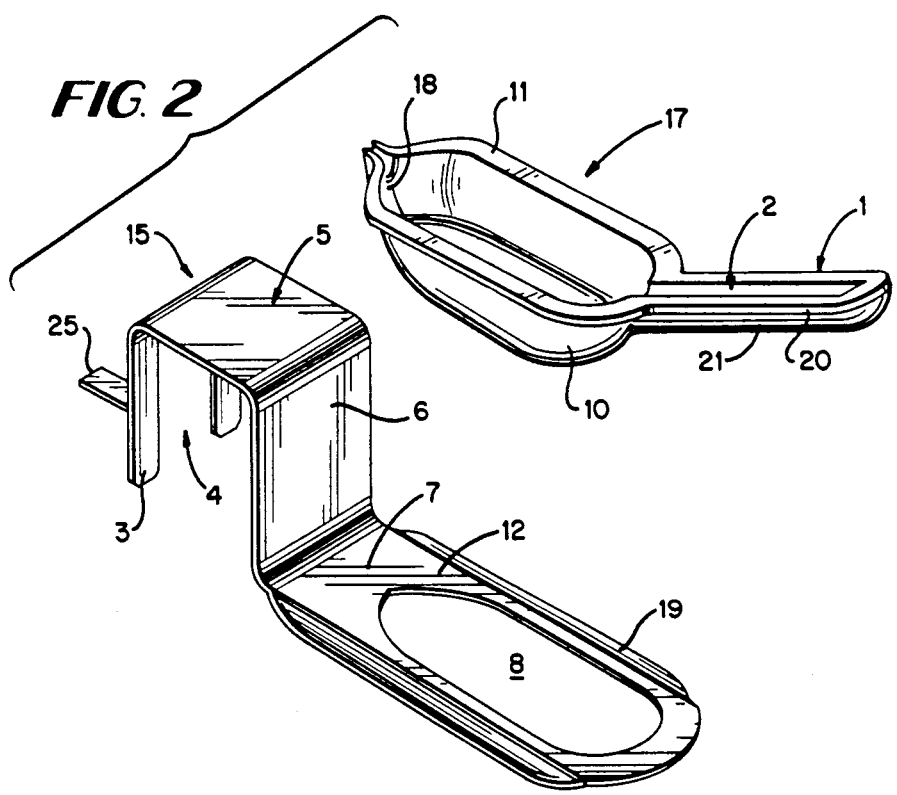
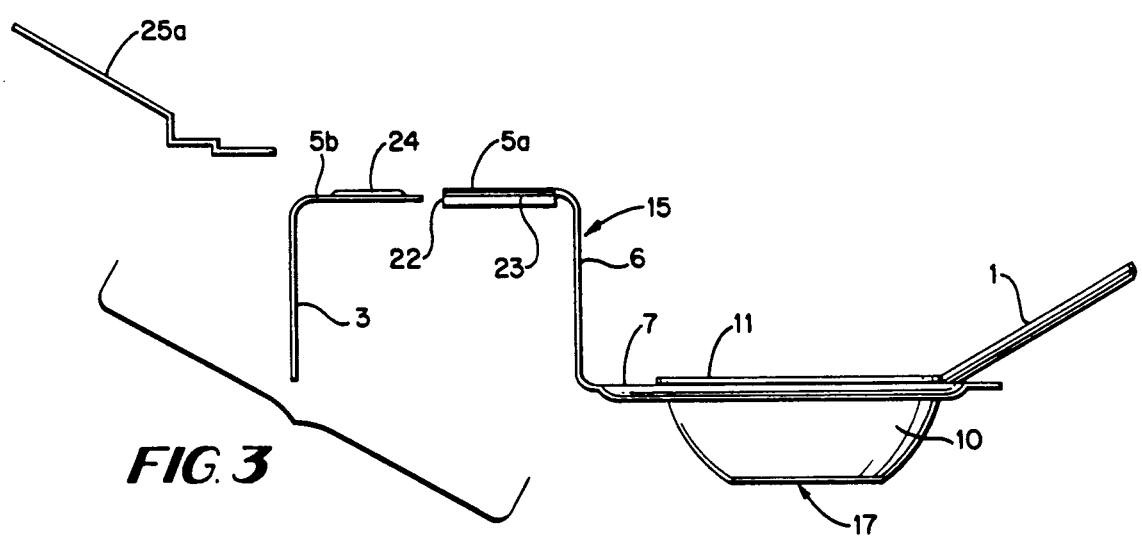

COMBINATION SPECIMEN CUP AND BRACKET

BACKGROUND OF THE INVENTION

PRIOR ART

This invention applies to brackets holding receivers and matching receivers.

More specifically, this invention applies to urine specimen collection.

The most significant patent related to this one is U.S. Pat. No. 3,625,654 issued to Van Duyne, which shows a specimen cup with a handle for being held by the user. Other patent show specimen cups which have a collection chamber attached below the receiving section of the specimen cup, such as U.S. Pat. No. 4,832,046. Several patents in the prior art show the use of a handle on a specimen cup.

Unlike the prior art identified, the present invention utilizes a bracket mechanism designed to hold in an unobtrusive manner a specimen cup so that the user does not actually need to handle the specimen cup during the time that the specimen is being received. The specimen cup handle cooperates with the bracket by funneling fluids within the reservoir of the specimen cup.

It is difficult for female users to hold a specimen cup while giving urine samples. It is a very uncomfortable situation for a user to have to handle a specimen cup due to the potential difficulty in holding the specimen cup in place, the difficulty in seeing the specimen cup in place, and the potential for soiling the user's hands when the specimen cup is held in place.

It is therefore one purpose of this invention to provide a bracket for holding specimen cups in an appropriate position so that a user sitting on a toilet seat does not need to hold the specimen cup in place.

It is another purpose of this invention to provide a specimen holder which funnels the sample within the main reservoir of the specimen cup while maintaining an unsoiled handle for removing the same.

It is another purpose of this invention to provide a holder for a specimen cup so that after the specimen is collected, it is not accidentally spilled when being retrieved by the user.

It is another purpose of this invention to provide a urine specimen holder and a bracket for same which allows urine specimens to be easily collected.

It is another purpose of this invention to provide a urine specimen holder and bracket which is easily cleaned.

These and other objects and advantages to the invention will become better understood hereinafter from a consideration of the specification, with reference to the accompanying drawings forming a part thereof and in which like numerals correspond to parts throughout the several views of the invention.

BRIEF DESCRIPTION OF THE DRAWINGS

For a further understanding of the nature and objects of the present invention, reference should be made to the following detailed description taken in conjunction with the accompanying drawings in which like parts are given like reference numerals and wherein:

FIG. 2 is a perspective view of the invention showing the individual components of the specimen cup and bracket.

FIG. 3 is a side elevation of the invention showing an alternate embodiment of the ledge.

GENERAL DISCUSSION OF THE INVENTION

The use of urine specimen collectors has always been a major part of medicine as a way of testing what is occuring internally to a patient.

The present invention is designed facilitate this process which has become even more important today as regular urine test sampling has become a part of health diagnosis and employee management.

The present invention seeks to simplify the taking of urine specimens from a female user by preventing the need for the female user to hold the specimen cup in place during the collection process and preventing the user from being required to hold the specimen contained in an upright manner until it can be set aside. The invention does this by providing for a specimen holder which is designed to fit within a bracket, which in turn in designed to hold the specimen container.

The specimen container is designed with a handle which is angled upward from the actual container part of the specimen holder in order that the handle will receive as small an amount of the specimen as possible so that it will not become difficult to handle itself. The handle is shaped so that the majority of the sample is collected in the center, but provides for room for the sample to be drained through an overflow mechanism provided therein in the event that the specimen is greater in volume than the container portion of the specimen cup.

The bracket portion of the invention is designed to hold the specimen in a location so that the user can, in turn, position themselves so that the specimen container receives the majority of the specimen.

DETAILED DISCUSSION OF THE PREFERRED EMBODIMENT(S)

Figure 1:
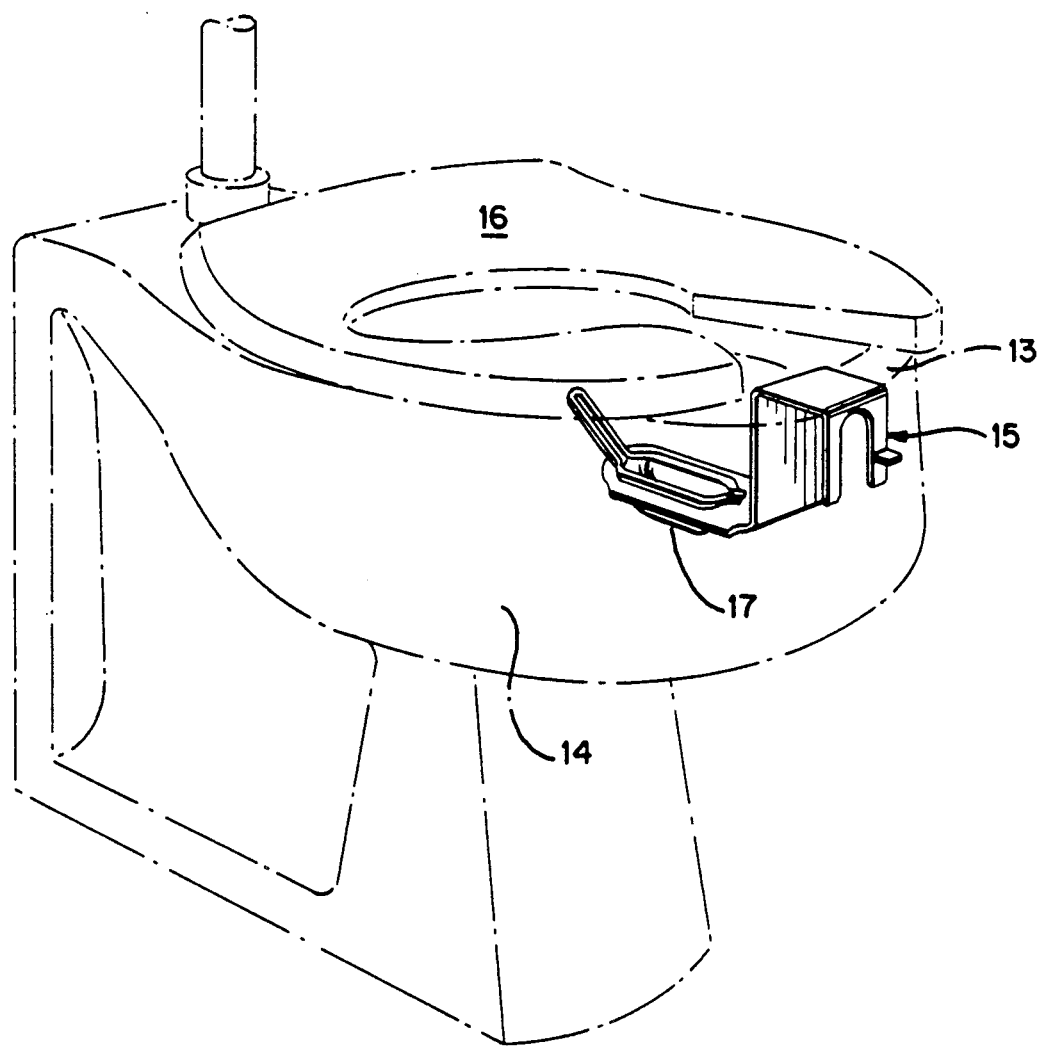
FIG. 1 is a perspective view of the invention shown in outline in place on a toilet.

As can best be seen from FIG. 1, the invention 15 is designed to fit onto a toilet bowl 14 having a rim 13. The invention comprises a bracket 15 which is firmly attachable to the toilet rim 13 by way of two bendable arms 3. The bendable arms 3 are separated by a space 4 which gives greater stability to the bracket than would be possible from a single arm.

The bendable arms 3 are necessary in order to provide for a curving bowl 14. Independent, spaced arms 3 allow for the bracket 15 to hold with stability curved surfaces of varying diameter of the various toilet bowls. The use of flexible materials allows the bracket 15 to be made in one unitary construction.

A handle 25 is provided in order to allow the device to be lifted without touching a part too closely associated with the bowl. In the preferred embodiment, handle 25 is located on one of the arms 3. An alternative embodiment would be to have the handle formed from the material between arms 3 which could be bent outward to provide a handle or inward to give additional holding power to the arms 3.

Since there are a variety of toilet bowls 14 only bendable arms 3 or highly flexible arms work well with the invention. Highly flexible materials tend to be heat sensitive or breakable.

Since the bracket 15 should be cleanable in either a centrifuge or high temperature environment to insure hygiene, metallic materials are preferred for the bracket. In order to assist in removal of the bracket with a limited amount of contamination, a bracket handle may be provided which extends out from the bracket away from the toilet bowl. When the entire bracket needs to be removed, the handle 25a could be inserted into a hole in the arm 3 and the entire device could be lifted. The bracket handle 25a could be designed to be removable to prevent the patient giving the sample from knocking the bracket by hitting the bracket handle.

The arms 3, in turn, are attached to a ledge 5, which runs along the top of the rim 13 for the width of the rim 13. A wall 6 then serves to lower the bracket 15 sufficiently so that it drops to the appropriate level below the toilet seat 16 so as not to interfere with the use of the toilet and to fit sufficiently low within the basin 14 for collection. A narrow plate 7 extends into the center of the bowl 14. The plate 7 is comprised of a band of metal with edges 19 on either side angled downward in order to prevent splashing and fluid accumulation in the event that the specimen contacts the plate 7 surface.

As can best be seen by reference to FIG. 3, an alternative embodiment is provided for the ledge. In this embodiment, the ledge comprises two parts. The first part has an upper ledge 5(a) has side walls 23 which define a slot 22 to recieve the second part. The second part has a lower ledge 5(b) that fits within the upper ledge within the slot 22 and defines a raised embossment 24. The embossment 24 serves to frictionally contact the top of upper ledge 5(a) to hold the bracket in place.

This design allows for the ledge 5 to be lengthened or shortened in order to fit different width toilets to prevent an inordinant amount of bending of arms 3 to have the device fit.

The forward end of the plate 7 is a recessed area 12 defining an opening 8 for receiving a specimen cup 17. The specimen cup 17 is described in more detail below. The opening 8 is shaped so as to accommodate a cup 17 having spout 18 shaped end. The outer edges 19 of the plate 7 are also angled downward to prevent splashing.

The specimen cup comprises a handle 1 having a base 20 and two sides 21 which in turn define a duct 2. The duct 2 is provided to guide any fluids touching the handle downward into the specimen cup reservoir 10 and to lend inflexibility to the handle 1. The duct 2 within the arm 1 is sufficient so that the hand of the user does not need to touch the base 20 of the duct 2 when the device is held. The handle is angled up 30° in order to keep at least the top of the handle 1 out of contact with the specimen and the bracket 15.

The base 20 feeds directly into the reservoir 10. The two sides 21 flow into a lip 11. Lip 11 surrounds the upper edge of the reservoir 10. The lip 11 is designed to receive the handle sides 21 to prevent loss of the specimen. The lip 11 is wider than the reservoir 10 and the width of opening 8. The reservoir 10 is more narrow than the width of the opening 8. Hence, the reservoir 10 may fit within the opening 8 while the lip 11 contacts the edges of the plate 12 of the bracket 15 and holds the reservoir 10 in place.

The specimen cup reservoir 10 is attached to the base 20 and the lip 11. In the preferred embodiment, the reservoir 10 is an integral part of the lip 11, and both are made of biodegradable material so that the entire specimen cup may be disposed of after each use. The end of the lip 11 and reservoir 10 opposite the attachment of the arm 1 define a spout 18. The spout 18 may be lower than the remainder of the lip 11 to act as an overflow. In the event this is desired, hole 8 would provide additional space for drainage of fluid coming out of the spout 18.

The reservoir 10 has a flat bottom so that when removed from the bracket it can sit upright on a flat surface.

Figure 4:
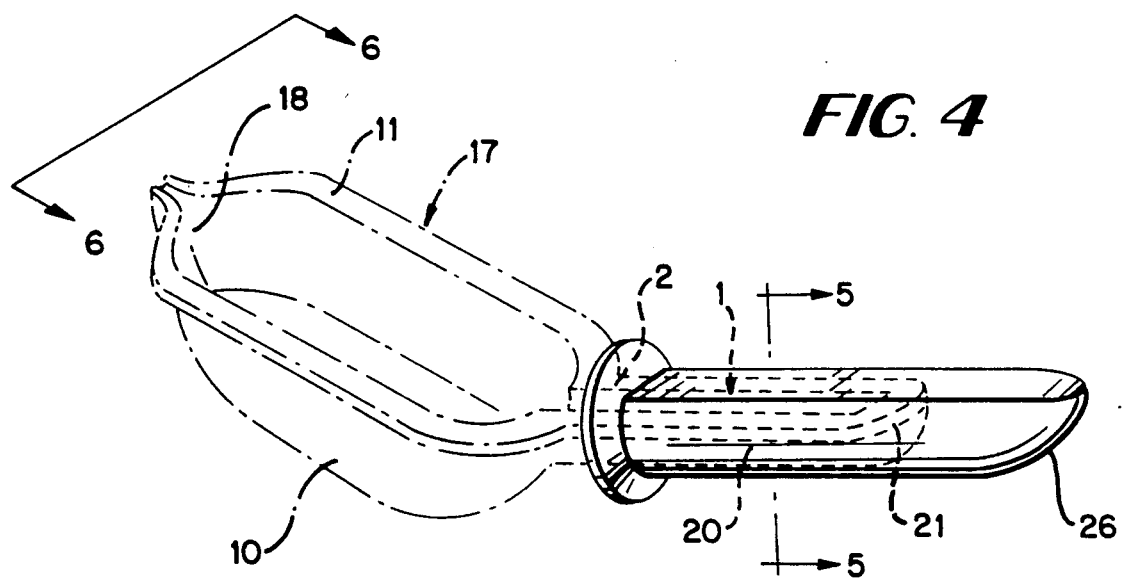
FIG. 4 shows an embodiment of the specimen cup in dotted lines being operated in conjunction with a specimen test tube vile.
Figure 6:
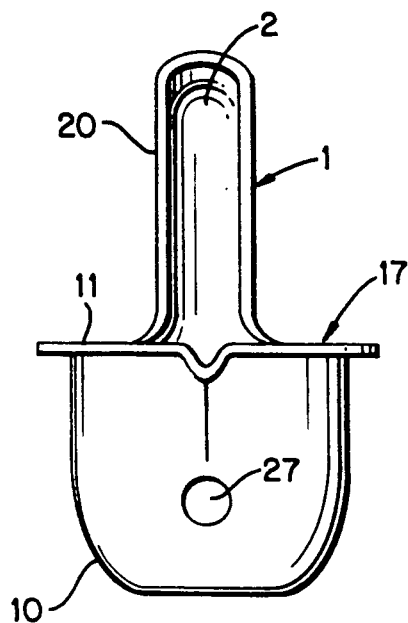
FIG. 6 is a front view of the specimen cup along line 6—6.

In the preferred embodiment, as shown in FIG. 6, the reservoir 10 is equipped with a drain 27. The level of the resevoir 10 below the drain 27 makes a defined volume. As shown in FIG. 4, specimen tube 26 of volume equal to or greater than the defined volume is made to slip over handle 1. In this way, the specimen tube 26 may be slipped over the handle 1 when the specimen of defined volume has been retrieved in the reservoir 10. The specimen and reservoir 10 may be lifted by tilting back the tube 26 and the specimen may be transferred to the tube 26 by tilting the tube back, which tilts, in turn, the handle 1 and reservoir 10 so that the specimen flows into the handle 1 and then into the tube 26. The specimen cup may then be disposed of.

Figure 5:
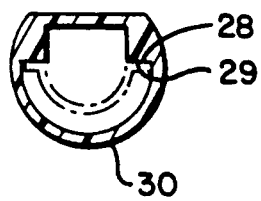
FIG. 5 is a cross section of FIG. 4 along line 5—5.

In an alternative embodiment, shown in cross section in FIG. 5, the tube 26 has a curved surface 30 conforming in shape to the two sides 21 and base 20 of the handle 1. The tube 26 also has a roof 28 which contacts the top 29 of handle sides 21. This shape prevents the specimen cup 17 from turning while the specimen is being transferred. In this way when the specimen tube 26 is inserted over the handle 1, in the preferred embodiment, the handle 1 is firmly held and cannot twist within the specimen tube 26.

The specimen tube 26 may have a fluted top to reduce spilling.

In use, the arms 3 are bent to be slightly so that the distance between the arms 3 and the vertical wall is slightly less than the width of the toilet bowl rim. The bracket is fitted onto the rim 13 of the toilet bowl 14. The arms 3, being bendable, bend to allow the bracket to fit onto the rim tightly. If a bracket handle 25a is used, then it may be removed at this time.

The arms 3 extend sufficiently far down so that they supply support to the entire bracket so the bracket sits steadily on the rim. Because the arms 3 in the preferred embodiment are made of a slightly malleable material that tends slightly to return to its existing shape, by bending the arms 3 in slightly more than the rim 13, the entire bracket 15 can be made to clip tightly into place on any size toilet.

The bracket ledge is flat and contacts the flat rim 13. The back end of the ledge 5 is slightly higher than the end which sticks into the toilet bowl 14, so that any drainage tends to be towards the toilet bowl 14.

In the preferred embodiment, and for most toilets, the arms 3 are approximately three inches (3") in length, the ledge 5 is approximately two inches (2") in length. The upper ledge 5(a) is two inches (2") and the lower ledge 5(b) is also two inches (2"). The wall 6 is approximately three inches (3") long, and the spacer 7 is approximately one and one-half inches (1½") in length. The opening for receiving the specimen cup 8 is approximately four and one half inches (4½") in length, and there is approximately five-sixteenths inch (5/16") of height opposite the shelf on the spacer 7. Once the bracket 15 is in place, an individual user may put the specimen cup in place with the arm 1 facing opposite the wall 6.

Because many varying and different embodiments may be made within the scope of the inventive concept herein taught, and because many modifications may be made in the embodiments herein detailed in accordance with the descriptive requirements of the law, it is to be understood that the details herein are to be interpreted as illustrative and not in a limiting sense.

What is claimed:

1. A specimen cup and bracket for the same for use on a toilet having a bowl and a rim:
   a. said bracket comprising at least one bendable arm engaging the side of said bowl, a ledge attached to said arm, a wall attached to said ledge opposite and a plate attached to said wall defining a hole for receiving the specimen cup, wherein the plate has edges angled downward from parallel;
   b. said specimen cup comprising a handle extending towards the bowl, said handle having a channel means for funneling fluid and a reservoir attached to the handle.

2. The invention of claim 1 wherein the specimen cup handle further comprises:
   a. a base;
   b. two walls attached to and extending upwardly from said base, said walls and base form a channel means for funneling fluid through the handle and to or from the reservoir.

3. The invention of claim 1 wherein the reservoir defines a spout at the end facing the toilet rim.

4. The invention of claim 1 wherein the reservoir further comprises a lip attached to the top of the reservoir and where the reservoir is smaller than the hole defined by the bracket and the lip is larger than the hole defined by the bracket.

5. The invention of claim 4 wherein the specimen cup handle further comprises:
   a. a base attached to the reservoir;
   b. two walls running substantially the length of said base and opposite one another and also attached to the reservoir, said walls and base forming a channel means for funneling fluid from the handle to the reservoir.

6. A specimen cup and bracket mounted on the rim of a toilet having inner and outer surfaces bridged by a ledge surface, said bracket comprising:
   a. at least one bendable arm, adapted to extend down the outer surface of said rim;
   b. a ledge attached to said arm, adapted to overlie said ledge surface;
   c. a wall attached to said ledge opposite said arm, adapted to extend down the inner surface of said rim;
   d. a plate attached to said wall and defining a hole for receiving the specimen cup, wherein the edges of said plate are slanted downwardly to drain fluid into the toilet.

7. A specimen cup and bracket for the same for use on a toilet having a bowl and a rim having inner and outer surfaces bridged by a ledge surface said bracket comprising:
   a. at least one bendable arm, adapted to extend down the outer surface of said rim;
   b. a ledge attached to said arm, adapted to overlie said ledge surface;
   c. a wall attached to said ledge opposite said arm, adapted to extend down the inner surface of said rim;
   d. a plate attached to said wall and being substantially horizontal to the ledge surface defining a hole for receiving the specimen cup, wherein the plate has side edges angled downward from said hole.

8. The invention of claim 7 wherein the ledge further comprises:
   a. an upper ledge having two side walls which define a slot, and
   b. a lower ledge designed to fit within the slot defined by the upper ledge in frictional contact therewith.

9. The invention of claim 6 wherein said ledge further comprises:
   a. an upper ledge defining a vertical slot;
   b. a lower ledge insertable within the vertical slot, and
   c. a raised embossment formed on the lower ledge so that when the lower ledge is inserted within the vertical slot, the raised embossment is in frictional contact with the upper ledge.

10. A specimen cup having a reservoir and bracket for said cup for use on a toilet having a bowl and a rim having inner and outer surfaces bridged by a ledge surface said bracket comprising:
    a. at least one bendable arm, adapted to extend down the outer surface of said rim;
    b. a ledge attached to said arm, adapted to overlie said ledge surface;
    c. a wall attached to said ledge opposite said arm, adapted to extend down the inner surface of said rim;
    d. a plate attached to said wall defining a hole for receiving the specimen cup, wherein said hole is longer than the reservoir.

11. A bracket for holding a specimen cup designed to fit onto a toilet bowl having a rim with inner and outer surfaces bridged by a ledge surface, said bracket comprising:
    a. two bendable arms separated by a space and adapted to extend down the outer surface of said rim;
    b. a ledge attached to the arms which runs along the top of the rim;
    c. a bracket handle attached to said bracket which extends out from the bracket away from the toilet bowl;
    d. a wall attached to the ledge which drops along the inner surface of the rim to the appropriate level below the toilet seat so as not to interfere with the use of the toilet when said bracket is holding a specimen cup within the bowl for collection, and
    e. a plate attached to the wall having edges on either side angled downward in order to prevent splashing and defining an opening for receiving the specimen cup.

12. A bracket for holding a specimen cup designed to fit onto a toilet bowl having a rim with inner and outer surfaces bridged by a ledge surface, said bracket comprising:
    a. two bendable arms separated by a space and adapted to extend down the outer surface of said rim;
    b. a ledge attached to the arms which runs along the top of the rim for the width of the rim;

c. a bracket handle attached to said bracket which extends out from the bracket away from the toilet bowl;

d. a wall attached to the ledge which drops along the inner surface of said rim to the appropriate level below the toilet seat so as not to interfere with the use of the toilet when said brackket is holding a specimen cup within the bowl for collection, and e. a plate attached to the wall having edges on either side angled downward in order to prevent splashing and defining an opening for receiving the specimen cup, wherein said bracket handle is removable from the bracket.

13. A bracket for holding a specimen cup designed to fit onto a toilet bowl having a rim with inner and outer surfaces bridged by a ledge surface, said bracket comprising:

a. two bendable arms separated by a space, and adapted to extend down the outer surface of said rim;

b. a ledge attached to the arms which runs along the top of the rim for the width of the rim;

c. a bracket handle attached to said bracket which extends out from the bracket away from the toilet bowl;

d. a wall attached to the ledge which drops along the inner surface of said rim to the appropriate level below the toilet seat so as not to interfere with the use of the toilet when said bracket is holding a specimen cup within the bowl for collection, and e. a plate attached to the wall having edges on either side angled downward in order to prevent splashing and defining an opening for receiving the specimen cup, wherein said opening in said plate is shaped so as to accommodate a specimen cup having a spout shaped end.

14. A specimen cup for insertion into an opening in a bracket attached to a toilet rim, said cup comprising:

a. a handle having a base and two sides which define a duct, said handle extending towards the toilet bowl, and b. a reservoir attached to said handle communicating with the duct.

15. A specimen cup for insertion into an opening in a bracket attached to a toilet rim, said cup comprising:

a. a handle having a base and two sides which define a duct, said handle extending towards the toilet bowl, and b. a reservoir attached to said handle communicating with the duct, wherein the handle is angled up from being level by at least ten degrees.

16. The specimen cup of claim 14 wherein said handle feeds fluid directly into or out of the reservoir.

17. The specimen cup of claim 14 wherein the two sides of said handle are attached to a lip on an upper edge of said reservoir.

18. The specimen cup of claim 17 wherein the lip receives the handle sides and the specimen cup reservoir is attached to the base to prevent loss of the specimen.

19. A specimen cup for insertion into an opening in a bracket attached to a toilet rim, said cup comprising:

a. a handle having a base and two sides which define a duct, and b. a reservoir attached to said handle communicating with the duct, wherein the two sides of said handle are attached to a lip on an upper edge of said reservoir, wherein the lip is wider than the reservoir and the width of said bracket opening, and wherein the reservoir is more narrow than the width of said bracket opening.

20. The specimen cup of claim 17 wherein the specimen cup is made of biodegradable material.

21. The specimen cup of claim 14 wherein the end of the reservoir opposite the handle defines a spout.

22. The specimen cup of claim 21 wherein the spout is lower than the remainder of the reservoir lip.

23. The specimen cup of claim 21 wherein the reservoir has a flat bottom.

24. The invention of claim 5 wherein the reservoir defines drain above the level of the bottom of the reservoir so that a defined volume is below the drain in the reservoir.

25. An apparatus for use on a toilet having a bowl and a rim comprising:

a. a bracket for mounting on said rim and defining a hole for receiving a specimen cup;

b. said specimen cup comprising a reservoir having a lip attached to the top of the reservoir, where said reservoir being smaller than the hole defined by the bracket and said lip being larger than the hole defined by the bracket, a handle having a base and two walls attached to the reservoir, the two walls running substantially the length of said base and opposite one another, said walls and base form a channel from the handle to the reservoir, and a drain above the level of the bottom of the reservoir so that a defined volume of liquid is retained below the drain in the reservoir; and c. a specimen tube having a tube volume at least equal to said defined volume and said specimen tube is inserted over the handle of the specimen cup.

26. The invention of claim 25 wherein a portion of the specimen tube is in frictional contact with the walls and base of the handle.

27. The invention of claim 25 wherein the handle walls further comprise tops and the specimen tube further defines a roof which contacts the tops of the handle walls and the specimen tube also defines a surface which matches the shape of and contacts the sides and base of the handle so that when the specimen tube is inserted over the handle, the handle is firmly held and cannot twist within the specimen tube.

28. A specimen cup for use with a bracket attached to a toilet, said specimen cup comprising:

a reservoir for receiving urine from a person using the toilet;

a handle extending from said reservoir, said handle comprising a duct along the length of the handle for allowing urine to flow from the reservoir and into a receiving container.

29. A specimen cup as in claim 28 wherein said duct comprises a channel for urine flowing from said reservoir.

30. A specimen cup as in claim 28 wherein said reservoir has a drain hole position so as to retain only a predetermined amount of urine in said reservoir.

31. A specimen cup as in claim 28 further comprising a lip on the upper edge of said reservoir and extending at least partially around the periphery of said reservoir, said lip engaging said bracket to support said cup when resting in said bracket.

32. A specimen cup as in claim 31 wherein a portion of said lip is separated from said bracket to allow excess urine to drain in a gap between said bracket and lip.

* * * * *